(12) United States Patent
Leonardi et al.

(10) Patent No.: US 7,683,179 B2
(45) Date of Patent: Mar. 23, 2010

(54) LERCANIDIPINE SALTS

(75) Inventors: Amedeo Leonardi, Milan (IT); Gianni Motta, Barlassina (IT); Markus von Raumer, Arlesheim (CH)

(73) Assignee: Recordati Ireland Limited, Milan (IT)

( * ) Notice: Subject to any disclaimer, the term of this patent is extended or adjusted under 35 U.S.C. 154(b) by 1118 days.

(21) Appl. No.: 11/211,769

(22) Filed: Aug. 24, 2005

(65) Prior Publication Data

US 2006/0047125 A1   Mar. 2, 2006

Related U.S. Application Data

(60) Provisional application No. 60/604,149, filed on Aug. 24, 2004.

(51) Int. Cl.
*C07D 213/80* (2006.01)
(52) U.S. Cl. .................................................. 546/321
(58) Field of Classification Search ........................ None
See application file for complete search history.

(56) References Cited

U.S. PATENT DOCUMENTS 4,705,797 A    11/1987   Nardi

| 4,968,832 A | 11/1990 | Bianchi |
| 5,696,139 A | 12/1997 | Leonardi |
| 5,767,136 A | 6/1998 | Sartani |
| 5,912,351 A | 6/1999 | Leonardi |
| 6,852,737 B2 | 2/2005 | Bonifacio et al. |
| 2003/0069285 A1 | 4/2003 | Leonardi et al. |

FOREIGN PATENT DOCUMENTS

| WO | 97/03669 | 2/1997 |
| WO | 99/67231 | 12/1999 |
| WO | 2004/035051 | 4/2004 |

OTHER PUBLICATIONS

International Search Report and Written Opinion mailed Nov. 11, 2005 in PCT/EP2005/009043.

*Primary Examiner*—Zinna N Davis
(74) *Attorney, Agent, or Firm*—Darby & Darby

(57) ABSTRACT

The present invention relates to new addition salts of lercanidipine comprising lercanidipine and an acid counterion wherein the acid counterion is selected from the group consisting of: (i) inorganic acids, (ii) sulfonic acids, (iii) monocarboxylic acids, (iv) dicarboxylic acids, (v) tricarboxylic acids, and (vi) aromatic sulfonimides, with the proviso that said acid counterion is not hydrochloric acid.

34 Claims, 8 Drawing Sheets

US 7,683,179 B2

LERCANIDIPINE SALTS

This application claims the benefit of U.S. Provisional Patent Application No. 60/604,149, filed Aug. 24, 2005, which is hereby incorporated by reference in its entirety.

FIELD OF THE INVENTION

The present invention provides novel acid salts of lercanidipine, particularly amorphous and crystalline lercanidipine salts and processes for making the same. The present invention also provides novel amorphous and crystalline lercanidipine salts in hydrated and solvated forms. Additionally, the present invention provides pharmaceutical compositions containing the novel lercanidipine salts disclosed herein.

BACKGROUND OF THE INVENTION

Lercanidipine (methyl 1,1,N-trimethyl-N-(3,3-diphenylpropyl)-2-aminoethyl 1,4-dihydro-2,6-dimethyl-4-(3-nitrophenyl)pyridine-3,5-dicarboxylate) is a highly lipophilic dihydropyridine calcium antagonist with a long duration of action and high vascular selectivity. Lercanidipine is a high affinity competitive antagonist of the dihyropyridine subunit of the L-type calcium channel.

Lercanidipine is useful as an anti-hypertensive. Lercanidipine treatment lowers blood pressure by blocking calcium channels of arterial smooth muscle, thus decreasing peripheral vascular resistance. Lercanidipine produces no negative cardiac inotropism and only occasional, mild reflex tachycardia, generally of short duration. Lercanidipine has been approved for the treatment of hypertension in Europe and has been marketed since 1996 in several European countries under the trademark Zanidip™.

The hydrochloride salt of lercanidipine is commercially available from Recordati S.p.A. (Milan, Italy). Methods of making both lercanidipine free base and the lercanidipine hydrochloride salt along with methods of resolving lercanidipine into individual enantiomers are described in U.S. Pat. Nos. 4,705,797; 5,767,136; 4,968,832; 5,912,351; and 5,696,139, all of which are incorporated herein by reference.

A major disadvantage of the process of preparing lercanidipine, as it is described in U.S. Pat. No. 4,705,797, is that the disclosed cyclization reaction generates several by-products, which results in a lower yield for the desired product. U.S. Pat. No. 5,912,351 describes a simpler process for the preparation of lercanidipine hydrochloride. The process yields lercanidipine hydrochloride in an anhydrous non-hygroscopic crystalline form, avoiding the formation of unwanted by-products and need for subsequent purification on chromatography columns.

However, the isolation of lercanidipine hydrochloride in crystalline form is again quite complex. Additionally, the lercanidipine hydrochloride may exist as any one of at least four distinct polymorphs, each of which has distinct physical properties (see, U.S. Pat. No. 6,852,737 and U.S. Patent Publication No. 2003/0069285). Therefore, there is a need in the art for simpler processes of producing lercanidipine salts, especially crystalline lercanidipine salts. There is also a need for lercanidipine salts that have solubility and/or other physical properties that are distinct from, and preferably more desirable than, the previously isolated forms of lercanidipine hydrochloride, including, but not limited to, reduced inter-patient variability, reduced food effect, and little or no polymorphism.

SUMMARY OF THE INVENTION

The present invention provides novel acid addition salts of lercanidipine, including amorphous and crystalline lercanidipine salts and processes for making the same. The present invention also provides amorphous and crystalline lercanidipine in hydrated and solvated forms. Additionally, the present invention provides pharmaceutical compositions containing the novel lercanidipine salts disclosed herein.

In one aspect, the invention provides for novel acid salts of lercanidipine, wherein the acid counterion is provided by an acid selected from the group of acids consisting of
 (i) inorganic acids, other than hydrochloric acid, such as hydrobromic acid, phosphoric acid and sulfuric acid;
 (ii) sulfonic acids, such as methanesulfonic acid, benzenesulfonic acid, toluenesulfonic acid, and napthalene-1,5,-disulfonic acid,
 (iii) monocarboxylic acids, such as acetic acid, (+)-L-lactic acid, DL-lactic acid, DL-mandelic acid, gluconic acid, cinnamic acid, salicylic acid, and gentisic acid,
 (iv) dicarboxylic acids, such as oxalic acid, 2-oxo-glutaric acid, malonic acid, (−)-L-malic acid, mucic acid, (+)-L-tartaric acid, fumaric acid, maleic acid, and terephthalic acid,
 (v) tricarboxylic acids, such as citric acid, and
 (vi) aromatic sulfonimides such as saccharin.

In another embodiment, the invention provides novel crystalline lercanidipine napadisylate, which has a melting point of about 150° C. (determined using differential scanning calorimetry, referred to herein as "DSC"), a solubility of about 3.5 mg/L in 0.1 M HCl at 22° C. and comprises about 3-4% (w/w) methanol.

In an additional embodiment, the invention provides novel crystalline lercanidipine besylate which has a melting point of about 172° C. (DSC peak), a solubility of about 87 mg/L in 0.1 M HCl at 22° C. and comprises about 0.1-0.2% (w/w) methanol.

In another embodiment, crystalline lercanidipine salts of the present invention may be present as polymorphs.

In another embodiment the present invention provides the foregoing group of lercanidipine salts in solvated and hydrated forms, particularly mono- and di-hydrates and solvates and more particularly mono- and dimethanolates.

In another embodiment methods are provided for the independent preparation of novel acid salts of lercanidipine, including both amorphous and crystalline lercanidipine salts, from lercanidipine free base as the starting material.

The invention further provides methods of preparing the foregoing salts, in amorphous and crystalline forms. In certain embodiments, the invention provides methods of crystallizing lercanidipine besylate and napadisylate and the crystalline salts obtained by such methods.

Also provided are pharmaceutical compositions comprising (1) at least one lercanidipine salt, other than lercanidipine hydrochloride, wherein the lercanidipine salt is selected from the foregoing group and combinations thereof with lercanidipine hydrochloride wherein content of each form is predetermined, and (2) at least one component selected from the group consisting of a pharmaceutically acceptable carrier, a diluent, a flavorant, a sweetener, a preservative, a dye, a binder, a suspending agent, a dispersing agent, a colorant, a disintegrant, an excipient, a lubricant, a plasticizer, and an edible oil.

In further embodiments the aforementioned pharmaceutical compositions are provided as dosage forms comprising one or more amorphous salts of the present invention and/or crystalline lercanidipine napadisylate and/or crystalline lercanidipine besylate and various solvated, hydrated and anhydrous forms thereof, optionally in combination with the hydrochloride salt of lercanidipine or the lercanidipine free base, or with other active ingredients such as angiotensin II receptor blockers and/or angiotensin converting enzyme inhibitors and/or diuretics.

These and other aspects of the present invention will be apparent to those of ordinary skill in the art in light of the present description, claims and figures.

DETAILED DESCRIPTION OF THE INVENTION

Figure 1:
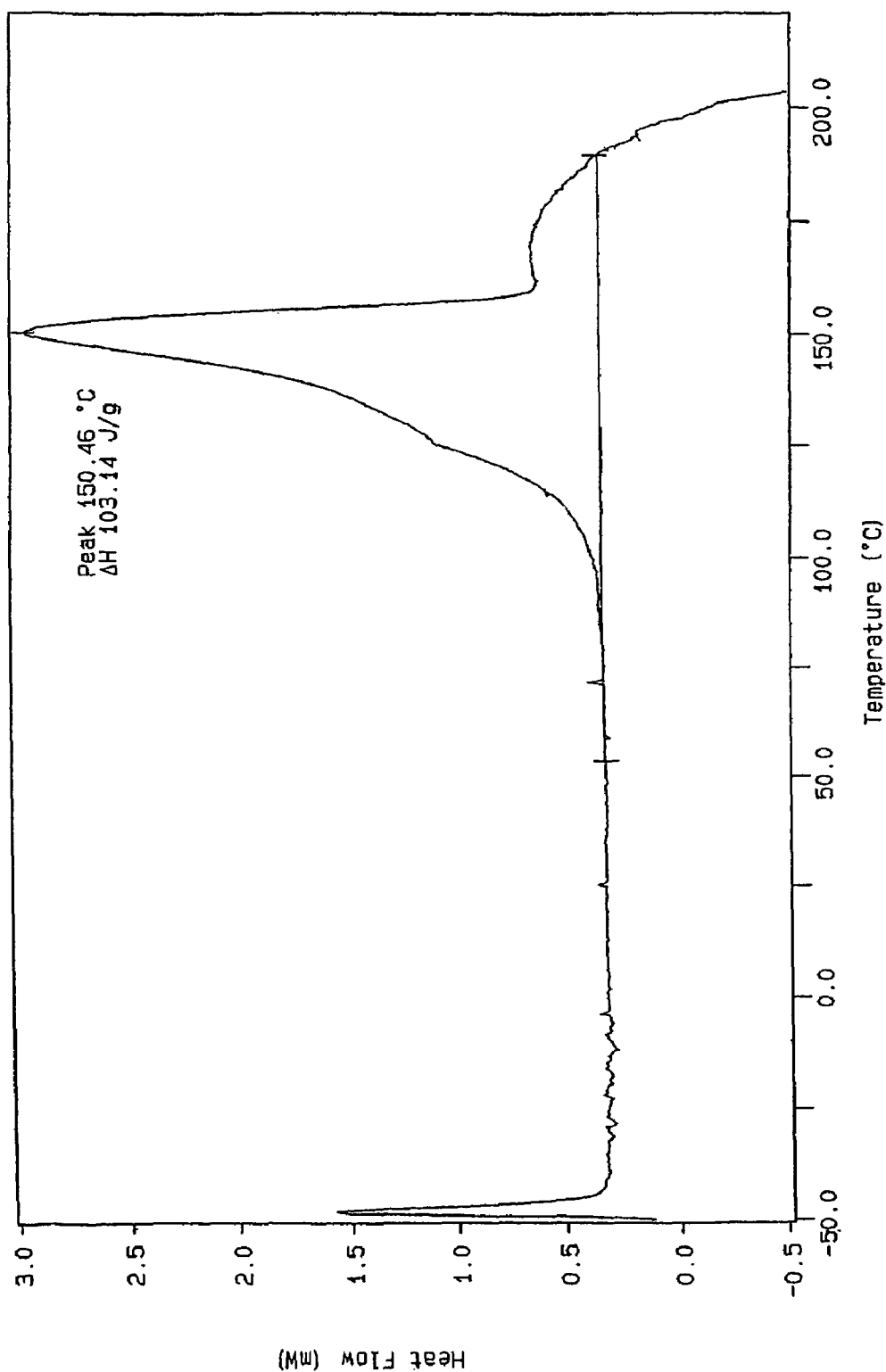
FIG. 1 depicts a differential scanning calorimetry profile for crystalline lercanidipine napadisylate.

The term "about" generally means within 10%, preferably within 5%, and more preferably within 1% of a given value or range. Alternatively, the term "about" means within an acceptable standard error of the mean, when considered by one of ordinary skill in the art. One of ordinary skill in the art can readily determine which definition of "about" applies from the context of its usage.

As used herein, the term "amorphous" refers to compounds having no substantial crystal lattice structure. Amorphous compounds typically yield DSC plots with broad endothermic transitions, defined as glass transitions. Crystalline compounds, by comparison, typically exhibit sharp endothermic peaks.

As used herein, the term "crystalline" refers to crystals of a compound having a melting point and x-ray spectra characteristic of crystalline forms. These compounds present DSC plots with characteristic sharp enodothermic peaks. Unless specifically stated otherwise, the term "crystalline forms" includes crystalline lercanidipine besylate and napadisylate salts.

As used herein, the term "lercanidipine" refers to methyl 1,1,N-trimethyl-N-(3,3-diphenylpropyl)-2-aminoethyl 1,4-dihydro-2,6-dimethyl-4-(3-nitrophenyl)pyridine-3,5-dicarboxylate, occurring as a free base or as a salt associated with a counterion.

As used herein, the term "lercanidipine besylate" refers to the acid salt of lercanidipine comprising methyl 1,1,N-trimethyl-N-(3,3-diphenylpropyl)-2-aminoethyl 1,4-dihydro-2, 6-dimethyl-4-(3-nitrophenyl)pyridine-3,5-dicarboxylate and a benzenesulfonic acid counterion in 1 to 1 ratio.

As used herein, the term "lercanidipine napadisylate" refers to the acid salt of lercanidipine comprising methyl 1,1,N-trimethyl-N-(3,3-diphenylpropyl)-2-aminoethyl 1,4-dihydro-2,6-dimethyl-4-(3-nitrophenyl)pyridine-3,5-dicarboxylate and the naphthalene-1,5-disulfonic acid counterion in a 2 to 1 ratio.

As used herein, the term "polymorphic" or "polymorphism" refers to a property of a crystalline compound to exist in two or more forms with distinct structures. The different crystalline forms can be detected directly by crystallographic techniques or indirectly by assessment of differences in physical and/or chemical properties associated with each particular polymorph.

The present invention discloses novel crystalline and amorphous acid salts of lercanidipine. In particular, the present invention provides crystalline lercanidipine besylate and napadisylate. The novel crystalline lercanidipine salts of the present invention may occur in one or more polymorphic forms. The present invention also provides several lercanidipine salts which, surprisingly, are essentially free of crystalline material.

The present invention also discloses novel solvated and hydrated forms of the crystalline and amorphous lercanidipine salts disclosed herein. Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of lercanidipine salsts are within the scope of the invention. Lercanidipine salts may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain, *Polymorphism in Pharmaceutical solids*. Marcel Decker, New York, 1999).

Solvated or hydrated forms of the lercanidipine salts of the present invention may be present as either mono- or di-solvates or hydrates. Solvates and hydrates may be formed as a result of solvents used during the formation of the lercanidipine salts becoming imbedded in the solid lattice structure. Because formation of the solvates and hydrates occurs during the preparation of a lercanidipine salt, formation of a particular solvated or hydrated form depends greatly on the conditions and method used to prepare the salt. Preferably the hydrated and solvated forms of the lercanidipine salts of the present invention include pharmaceutically acceptable solvents.

The novel lercanidipine acid salts of the present invention are preferably obtained from lercanidipine free base and may be prepared by adding a solution of an acid in a suitable solvent to a solution of the free base dissolved in a suitable solvent, followed by removal of the solvent(s). The novel crystalline lercanidipine salts preferably may be formed by adding a solution of the acid dissolved in a suitable solvent to a solution of the free base dissolved in a suitable solvent followed by recrystallization in at least two successive steps using aprotic and protic solvents. Further purification steps may include washing at different temperatures with different solvents or recrystallization from different or mixed solvents.

The novel amorphous and crystalline lercanidipine salts of the present invention have distinct chemical and physical properties, from one-another and from crystalline lercanidipine hydrochloride. The physical and chemical properties of the novel amorphous and crystalline salts of lercanidipine of the present invention, are discussed in detail below.

In certain preferred embodiments, the invention provides lercanidipine besylate and napadisylate salts. These crystalline lercanidipine salts forms can be isolated with a purity as high as 99.5% and a residual solvents content of <3000 ppm, but less pure (and/or with higher solvent or water content) forms can also be obtained by methods well known in the art. Pharmaceutically acceptable levels for each impurity are generally ≦0.1%; for organic solvents they range from 5000 ppm to 2 ppm depending on toxicity of each solvent. The lercanidipine salts of the present invention can be purified by crystallization from different solvents and the solvent content can be reduced by drying under controlled conditions or azeotropic removal.

Both crystalline besylate and crystalline napadisylate exhibit good stability. Preparation of crystalline besylate is characterized by the slow formation of crystals, and the production of high yields of crystals only after the addition of seeding crystals. Crystalline besylate is characterized by a pale yellow color, and has a smaller crystal size, higher solubility in 0.1N HCl and a higher melting point (DSC peak), compared to crystalline napadisylate. Crystalline besylate has a solubility in 0.1 N HCl at 22° C. from about 25 to about 35 mg/L and more specifically about 30 mg/L and does not exhibit polymorphism, i.e., exists in a single crystal form. The melting point (DSC Peak) of crystalline besylate is within the range of about 170° C. to about 175° C., more specifically, about 172° C.

Crystalline besylate and crystalline napadisylate, display physical characteristics distinct not only from one another, but also from previously isolated crystalline lercanidipine hydrochloride. Crystalline besylate has a solubility in 0.1 N HCl of about 30 mg/L, compared to the solubility of crystalline hydrochloride in the same media of about 10 mg/L. Crystalline napadisylate is less soluble then crystalline hydrochloride, displaying a solubility of about 3.5 mg/L in 0.1 N HCl.

Crystalline napadisylate is characterized by the spontaneous formation of crystals having a pale yellow color. Compared to crystalline besylate, crystalline napadisylate has lower solubility in 0.1 N HCl and a lower melting point. The crystalline napadisylate of the present invention has a solubility in 0.1 N HCl from about 3 mg/L to about 4 mg/L and more specifically about 3.5 mg/L. The melting point (DSC peak) of crystalline lercanidipine napadisylate is within the range of about 145° C. to about 155° C., more specifically about 150° C.

Crystalline napadisylate and crystalline besylate may be prepared as solvated hydrates or as anhydrous forms. Hydrated or solvated forms are obtained by recrystallization from polar solvents containing variable amounts of water, using techniques well known in the art. In preferred embodiments, crystalline lercanidipine napadisylate is prepared as a solvated hydrate, e.g., dimethanolate hydrate, or as an anhydrous form.

The physical and chemical properties of the amorphous lercanidipine salts of the present invention are distinct from both crystalline besylate and napadisylate salts, as well as from crystalline lercanidipine hydrochloride. Surprisingly, the amorphous lercanidipine salts are characterized by the absence of crystalline material, even after repeated crystallization attempts using a variety of solvents and crystallization conditions. The absence of crystalline material was confirmed by polarized microscopy, FT-Raman spectroscopy and DSC. Amorphous samples are characterized, e.g., as having no birefringency under cross polarizers, broad peaks in the FT-Raman spectrum, or a DSC curve having a broad endothermic transition, i.e., a glass transition and no distinct melting peak. The limits of detecting crystalline material in an otherwise amorphous composition using FT-Raman spectroscopy are generally from about 5 to about 10% of the sample (w/w) and the limit of detection using DSC is generally about 5 to about 10% of the sample (w/w).

Compared to crystalline lercanidipine salts, amorphous lercanidipine salts have a higher solubility in 0.1 N HCl and display DSC plots having broad endothermic transitions, i.e., glass transitions, rather than distinct phase transitions. The amorphous lercanidipine salts of the present invention also have FT-Raman spectra which are distinct from both the novel crystalline salts of the present invention and from those of crystalline lercanidipine hydrochloride.

The crystalline lercanidipine salts of the present invention may be prepared in substantially pure form with little residual solvent. Particularly, crystalline lercanidipine besylate may be prepared such that residual solvent content is from about 0.1 to about 0.5% (w/w) mass and more particularly less than about 0.2% (w/w) mass. Crystalline lercanidipine napadisylate may be prepared such that residual solvent content is from about 2.5 to about 5% (w/w) and more particularly less than about 4% (w/w).

The present application further discloses pharmaceutical formulations and unit dosage forms that comprise one of the novel lercanidipine salts of the present invention or a mixture of one or more of the presently disclosed lercanidipine salts.

Pharmaceutical Compositions

The novel lercanidipine salts of the present invention may be formulated into pharmaceutical compositions. According to the present invention, pharmaceutical compositions comprise at least one novel lercanidipine salt and an excipient or additive. Preferred excipients and additives include, but are not limited to pharmaceutically acceptable carriers or diluents, flavorants, sweeteners, preservatives, dyes, binders, suspending agents, dispersing agents, colorants, disintegrants, excipients, film forming agents, lubricants, plasticizers, edible oisl or any combination of two or more of the foregoing.

Both crystalline and amorphous salts of lercanidipine of the invention can undergo micronization, using methods well known in the art. Micronization may be performed, e.g., by a jet-mill process using a MICRONETTE M300 (NUOVA GUSEO, Villanova sull'Arda—PC—Italy). Parameters are as follows: Injection pressure, 5 Kg/cmq; micronization pressure, 9 Kg/cmq; and cyclone pressure, 2.5 Kg/cmq. Capacity of micronization is 16 Kg/h. Particle size is determined by laser light scattering using a GALAI CIS 1 laser instrument (GALAI, Haifa, Israel). Preferably micronization is performed to obtain an average particle size of about D(90%)<15 µm, and more preferably to obtain an average particle size of about D(90%)<15 µm, (50%)2-8 µm.

Suitable pharmaceutically acceptable carriers or diluents include, but are not limited to, ethanol, water, glycerol, propylene glycol, aloe vera gel, allantoin, glycerin, vitamin A and E oils, mineral oil, PPG2 myristyl propionate, magnesium carbonate, potassium phosphate, vegetable oil, animal oil, and solketal.

Suitable binders include, but are not limited to, starch, gelatin, natural sugars, such as glucose, sucrose and lactose, corn sweeteners, natural and synthetic gums, such as acacia, tragacanth, vegetable gum, and sodium alginate, carboxymethylcellulose, hydroxypropylmethylcellulose, polyethylene glycol, povidone, waxes, and the like. Preferred binders are lactose, hydroxypropylmethylcellulose and povidone.

Suitable disintegrants include, but are not limited to, starch (e.g., corn starch or modified starch) methyl cellulose, agar, bentonite, xanthan gum, sodium starch glycolate, crosspovidone and the like. A preferred disintegrant is sodium starch glycolate.

Suitable lubricants include, but are not limited to, sodium oleate, sodium stearate, sodium stearyl fumarate, magnesium stearate, sodium benzoate, sodium acetate, sodium chloride and the like. A preferred lubricant is magnesium stearate.

A suitable suspending agent is, but is not limited to, bentonite, ethoxylated isostearyl alcohols, polyoxyethylene sorbitol and sorbitan esters, microcrystalline cellulose, aluminum metahydroxide, agar-agar and tragacanth, or mixtures of two or more of these substances, and the like. A preferred suspending agent is microcrystalline cellulose.

Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin.

Suitable film forming agents include, but are not limited to, hydroxypropylmethylcellulose, ethylcellulose and polymethacrylates.

Suitable plasticizers include, but are not limited to, polyethylene glycols of different molecular weights (e.g., 200-8000 Da) and propylene glycol. Preferred is polyethylene glycol 6000.

Suitable colorants include, but are not limited to, ferric oxide(s), titanium dioxide and natural and synthetic lacquers. Preferred are ferric oxides and titanium dioxide.

Suitable edible oils include, but are not limited to, cottonseed oil, sesame oil, coconut oil and peanut oil.

Examples of additional additives include, but are not limited to, sorbitol, talc, stearic acid, dicalcium phosphate and polydextrose.

Unit Dosage Forms

Pharmaceutical compositions may be formulated as unit dosage forms, such as tablets, pills, capsules, caplets, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition. In general, any delivery of active ingredients that results in systemic availability of them can be used. Preferably the unit dosage form is an oral dosage form, most preferably a solid oral dosage form. Therefore, the preferred dosage forms are tablets, pills, caplets and capsules. Under certain circumstances, parenteral preparations may also be preferred, especially when oral administration is cumbersome or impossible.

Solid unit dosage forms may be prepared by mixing a lercanidipine salt of the present invention with a pharmaceutically acceptable carrier and any other desired additives as described above. The mixture is typically mixed until a homogeneous mixture of the lercanidipine salt and the carrier and any other desired additives is formed, i.e., until the lercanidipine salt is dispersed evenly throughout the composition. In this case, the compositions can be formed as dry or moist granules.

Tablets or pills can be coated or otherwise compounded to form a unit dosage form which has preferably, a modified release profile. For example, the tablet or pill can comprise an inner dosage and an outer dosage component, the latter being in the form of a layer or envelope over the former. The two components can be separated by a release modifying layer which serves to permit dissolution of the lercanidipine salt from the core component over a prolonged period of time. Alternatively, the lease modifying agent is a slowly disintegrating matrix. Additional modified release formulations will be apparent to those skilled in the art.

Biodegradable polymers for controlling the release of the lercanidipine salt include, but are not limited to, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

For liquid dosage forms, the lercanidipine salt is brought into solution, suspension or emulsion, optionally with the usually employed substances such as solubilizers, emulsifiers or other auxiliaries. Solvents for the preparation of liquid dosage forms, can include water, physiological salt solutions or alcohols, e.g. ethanol, propane-diol or glycerol. Additionally, sugar solutions such as glucose or mannitol solutions may be used. It is well understood among those of ordinary skill in the art that crystalline dosage forms may be retained in a solution, i.e., be present a suspension, by selecting appropriate solvents that do not result in dissolution of the crystalline form. A mixture of the various solvents mentioned may further be used in the preparation of liquid dosage forms.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontohoretic (electrical diffusion) delivery system. Transdermal dosage forms may be used for timed release and sustained release of the lercanidipine salts of the present invention.

Pharmaceutical compositions and unit dosage forms of the present invention for administration parenterally, and in particular by injection, typically include a pharmaceutically acceptable carrier, as described above. A preferred liquid carrier is vegetable oil. Injection may be, for example, intravenous, intrathecal, intramuscular, intraruminal, intratracheal, or subcutaneous.

Further, the lercanidipine salts of the present invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The crystalline lercanidipine salt compounds of the present invention may be coupled with soluble polymers as targetable drug carriers. Such polymers include, but are not limited to, polyvinyl-pyrrolidone, pyran copolymer, polyhydroxypropylmethacryl-amidephenol, polyhydroxy-ethylasparta-midephenol, and polyethyl-eneoxideopolylysine substituted with palmitoyl residues.

EXAMPLES

The following examples of preparation of acid salts of lercanidipine, are now disclosed for illustrative, non-limiting purposes. The preparation of both crystalline and amorphous lercanidipine salts are disclosed. Also disclosed are the results of various physical and chemical analysis of the novel lercanidipine salts of the present invention, including: elemental analysis, gravimetric analysis, hygroscopicity, X-ray diffraction, melting point, solubility analysis, and FT-Raman evaluation.

Example 1

Preparation of Amorphous Lercanidipine Besylate

A stock solution of lercanidipine free base was prepared by dissolving 181.7 mg of lercanidipine free base in 0.2 ml tetrahydrofuran (THF). The free base may be obtained by dissolving the crystalline lercanidipine hydrochloride (commercially available from Recordati S.p.A., Milan, Italy) in methanol, adding a slight excess of 2 N NaOH followed by water and filtering the obtained precipitate, which is then dried at room temperature under vacuum. An acid stock solution was prepared by dissolving 65.3 mg benzenesulfonic acid in 0.1 ml THF. An equimolar mixture of the lercanidipine stock solution (0.2 ml) and the acid stock solution (0.072 ml) was prepared. All of the solvent was removed under vacuum. Upon removal of the solvent a glassy film, characteristic of amorphous material, was observed. The amorphous material was dissolved in methanol (MeOH) and seeded with crystalline solid, resulting in a pale yellow crystalline material.

Several initial attempts, using various solvent combinations, were made to crystallize the amorphous lercanidipine besylate. None of these attempts were successful at forming crystalline lercanidipine besylate (the only two successful crystallizations of lercanidipine besylate are described below in Example 2, the second of which employs seeding using the product of the first method). The general experimental scheme for attempting to crystallize amorphous lercanidipine besylate involved: (1) dissolving about 35 mg amorphous lercanidipine besylate (prepared as described above) in about 0.5 ml of an organic solvent selected from MeOH, acetonitrile (MeCN), ethanol (EtOH), or dichloromethane ($CH_2Cl_2$), (2) slowly evaporating the solvent under ambient conditions for at least 20 days, (3) drying the sample completely under vacuum, (4) dissolving the sample in about 0.025 ml EtOH, and (5) storing the sample closed at $-18°$ C. for 5 days.

Example 2

Preparation of Crystalline Lercanidipine Besylate

A stock solution of lercanidipine free base was prepared by dissolving 212.3 mg of lercanidipine free base in 1 ml tetrahydrofuran (THF). An acid stock solution was prepared by dissolving 21.7 mg benzenesulfonic acid in 0.1 ml THF. A mixture of the lercanidipine stock solution (0.236 ml) and the acid stock solution (0.06 ml) was prepared and stored closed at 25° C. for 24 hours. The mixture was then stored at $-18°$ C. for 24 hours and at 25° C. for an additional 24 hours. No precipitate was observed at this point.

The solvent was allowed to evaporate under ambient conditions. After 4 days a glassy film was observed. The glassy film was dissolved in 0.15 ml ethyl acetate (EtAc). After 8 days no precipitate was observed. Again the solvent was evaporated and a glassy film developed. The glassy film was dissolved in 0.05 ml tert-butyl methyl ether (TBME) and the sample was allowed to stand closed at room temperature for 6 days. No precipitate was observed at this point.

An additional 0.05 ml TBME were added and the sample was subjected to temperature cycling (20-40-20° C., 5 cycles, 2 hours rise time and 2 hours fall time, 10 minutes isotherm periods at 20 and 40° C.). No precipitate was observed and the solvent was evaporated under a gentle nitrogen flow.

Following evaporation of the solvent, a sticky sample was obtained. The sample was stored under vacuum for 24 hours. The sample was suspended in 0.05 ml methanol (MeOH) and the sample was stored closed at 20° C. The sample produced a viscous liquid containing several solid particles. The sample was stored for an additional three days at 20° C. after which time the sample was completely solid and demonstrated a birefringency under crossed polarizers, confirming the presence of crystalline material.

The crystalline material was used as seeding material in a second experiment to obtain greater yields of crystalline lercanidipine besylate. Again stock solutions of lercanidipine free base (1.10 g free base dissolved in 2.2 ml MeOH) and acid (0.2844 g benzenesulfonic acid dissolved in 0.5 ml MeOH) were prepared and mixed together. Solvent was removed from the solution under a gentle nitrogen flow. When the solution volume had been reduced to 2 ml, crystalline lercanidipine besylate obtained as described above, was added to the solution. Again the solvent was removed under a gentle nitrogen flow, until the solution volume had been reduced to 1 ml. The sample was allowed to stand closed at room temperature for 7 days. The sample was filtered on a glass filter and dried under vacuum.

A final yield of 1.21 g, pale yellow, crystalline lercanidipine besylate was obtained. Elemental analysis revealed that the crystalline salt had a composition of $C_{42}H_{47}N_2O_9S$ (MW 755.9, non-solvated) which corresponds to a salt to free base ratio of 1:1 (mol/mol). The salt was non-solvated and non-hygroscopic and displayed a mass loss of 0.1% as determined by TG-FTIR.

A larger scale production has been performed as follows. A solution of 48 g of lercanidipine free base in 96 ml of methanol was added with 12.7 g of benzenesulfonic acid in 22 ml of methanol at room temperature. The resulting suspension was filtered and evaporated at 55° C. to a final volume of 50 ml. The solution was then seeded with crystalline lercanidipine besylate, and allowed to stand at room temperature for 24 hours, followed by storage at 5 C for 6 days. The resulting compact mass of crystals was collected by suction, washed with 2×40 ml of methanol and dried under vacuum in the presence of $P_2O_5$. 51.1 g of lercanidipine besylate was obtained.

Example 3

Preparation of Crystalline (and Amorphous) Lercanidipine Napadisylate

A stock solution of lercanidipine free base was prepared by dissolving 169.6 mg of lercanidipine free base in 0.82 ml methanol (MeOH). A solution was prepared by mixing 0.2 ml of the lercanidipine free base stock solution and 0.195 ml of aqueous naphthalene-1,5-disulfonic acid (50 mg/ml). Upon mixing, a precipitate was observed. The precipitate was dissolved by the addition of 1.0 ml MeOH. The sample was stored at $-18°$ C. for 4 days, with daily warming to room temperature for observation. The sample was then stored open at room temperature for seven days in order to allow the solvent to evaporate. Crystals were observed upon evaporation of the solvent. The crystals were suspended in 0.25 ml $H_2O$ and 0.01 ml MeOH. Following suspension, the crystals were collected by filter centrifugation (10,000 RPM, 0.22 μm filter) and dried under vacuum.

The crystalline material was used as seeding material in a second experiment in order to obtain even higher yields of crystalline lercanidipine napadisylate. A solution of lercanidipine free base was prepared by dissolving 1.1 g of lercanidipine free base in 4.4 ml MeOH. To the free base solution, 5.184 ml of aqueous naphthalenedisulfonic acid (50 mg/ml) was added and a precipitate immediately formed. The precipitate was dissolved upon the addition of 23 ml MeOH. The solution was seeded with crystalline material obtained above and the solution was stored at 4° C. for four days, followed by an additional three days at −18° C. Crystals were collected by filter centrifugation and dried under vacuum.

A final yield of 0.905 g, pale yellow, crystalline lercanidipine napadisylate was obtained. Elemental analysis revealed that the crystalline salt had a composition of $C_{82}H_{90}N_6O_{18}S_2$ (MW 1511.76, non-solvated) which corresponds to an acid to free base ratio of 1:2 (mol/mol). The salt occurred as a hydrated dimethanolate and displayed a total mass loss of 4.1% (0.4% $H_2O$ lose and 3.7% MeOH lose) as determined by TG-FTIR.

Amorphous lercanidipine napadisylate was produced by mixing 0.2 ml of the lercanidipine free base stock solution (prepared as described above) and 0.195 ml of aqueous naphthalene-1,5-disulfonic acid (50 mg/ml). Upon mixing, a precipitate was observed. The precipitate was isolated by rapid evaporation of the solvent under vacuum to yield amorphous lercanidipine napadisylate.

Example 4

Preparation of Amorphous Salts and Attempts to Form Additional Crystalline Lercanidipine Salts A salt screening was performed using a number of counterions and lercanidipine free base in order to determine which, if any, counterions were capable of producing crystalline lercanidipine salts. The screening experiments involved the investigation of eleven counterions; acetate, cinnamate, fumarate, L-lactate, DL-lactate, L-malate, maleate, DL-mandelate, mesylate, sulfate, and tosylate. Several crystallization attempts were made with each of the counterions. None of the counterions were capable of producing crystalline lercanidipine, even after several attempts. The general experimental scheme used in the screening of each of the eleven counterions is discussed in detail below. The choice of crystallization techniques was influenced by the known difficulty in obtaining crystalline lercanidipine and therefore, sufficient storage times and slow processes were chosen.

The final lercanidipine salts obtained from each of the salt screening experiments was dried completely and subjected to chemical and physical analysis. The chemical composition of each of the salt was determined by elemental analysis, thermogravimetric analysis coupled to infra-red spectroscopy, and water content analysis. The salts were also underwent physical testing using FT-Raman spectroscopy and were subjected to solubility testing.

Example 4a

Acid Dissolved in Tetrahydrofuran

Separate stock solutions of lercanidipine free base and respective acids were prepared by dissolving lercanidipine free base in tetrahydrofuran (THF) and the respective acid in THF is shown in Table 1.

TABLE 1

| Stock Solution | Solute | Solvent |
| --- | --- | --- |
| Lercanidipine | 212.3 mg lercanidipine free base | 1 ml THF |
| Cinnamate | 21.5 mg cinnamic acid | 0.1 ml THF |
| Maleate | 31.6 mg maleic acid | 0.2 ml THF |

Aliquots of lercanidipine free base and acid stock solution were mixed, accounting for the stereochemistry of the acids, as well as the molar ratios of acid to base. No precipitate was observed upon mixing of the stock solutions. Samples were stored closed for 24 hours at 25° C., followed by additional storage for 24 hours at 4° C. and 24 hours at −18° C. No solid was observed after storage.

Solvent was removed from the samples by evaporation under ambient conditions. After four days, a glassy film was observed. The glassy film was dissolved in acetone and allowed to stand at room temperature for two days. No precipitate was observed. Samples were allowed to stand for an additional six days and again no precipitate was observed.

Solvent was evaporated under a gentle nitrogen flow and a glassy film formed. The glassy film was dissolved in tert-butyl methyl ether (TBME) and the sample was allowed to stand at room temperature for six days. Additional TBME was added to the sample and the sample was subjected to temperature cycling (20-40-20° C., 5 cycles, 2 hours rise time and 2 hours fall time, 10 minutes isotherm periods at 20 and 40° C.). No solid was observed and again solvent was evaporated under a gentle nitrogen flow.

Following evaporation of the solvent, a sticky sample was obtained. The sample was stored under vacuum for 24 hours. The sample was suspended in methanol (MeOH) and the sample was stored closed at 20° C. The sample produced a sticky mass, however no crystalline material was observed. The sample was stored for an additional 24 hours under vacuum to remove the solvent. No crystalline material was observed following removal of the solvent.

The present example yielded two amorphous lercanidipine salts; lercanidipine cinnamate and lercanidipine maleate. Each amorphous lercanidipine salt was subjected to elemental analysis; thermogravimetric analysis coupled to infra-red spectroscopy; and water content analysis. Each amorphous lercanidipine salt also underwent physical testing using FT-Raman spectroscopy and was subjected to solubility testing. The results are described in Table 2, below.

TABLE 2

| Salt form | Proposed formula | Elemental Analysis | TG-FTIR (mass loss) | FT Raman spectrum | Solubility in 0.1 N HCl |
| --- | --- | --- | --- | --- | --- |
| Cinnamate | $C_{36}H_{41}N_3O_6 \cdot C_9H_8O_2 \cdot 0.2H_2O$ (0.47% $H_2O$) | Calcd %: C 70.8, H 6.5 N 5.5<br>Found %: C 70.7, H 6.4, N 5.5 | 0.3% ($H_2O$) | agrees with proposed structure | 89 mg/L |
| Maleate | $C_{36}H_{41}N_3O_6 \cdot C_4H_4O_4 \cdot 0.25MeOH$ | Calcd %: C 65.7, H 6.3, N 5.7<br>Found %: C 65.7, H 6.3, N 5.6 | 1.9% (MeOH) | agrees with proposed structure | 71 mg/L |

Example 4b

Counterion Dissolved in Methanol

Additional salt screening experiments were carried out by preparing separate stock solutions of lercanidipine free base and acid. Stock solutions were prepared by dissolving lercanidipine free base in TBME and the respective acid in MeOH (Table 3).

TABLE 3

| Stock Solution | Solute | Solvent |
| --- | --- | --- |
| Lercanidipine | 223.7 mg lercanidipine free base | 0.8 ml TBME |
| L-lactate | 14.6 mg L-lactic acid | 0.2 ml MeOH |

Aliquots of lercanidipine free base and acid stock solution were mixed, accounting for the stereochemistry of the acid, as well as the molar ratios of acid to base. No precipitate was observed upon mixing of the stock solutions. Samples were stored closed for 24 hours at 25° C., followed by additional storage for 8 hours at 60° C. and six days at 4° C. No solid was observed after storage.

Water was added to the sample, followed by evaporation of the solvent under ambient conditions. After four days, a glassy film was observed. The sample was stored under vacuum for 24 hours. The glassy film was dissolved in MeOH and stored closed for 24 hours at 20° C. After 24 hours a sticky mass was observed, but no solid particles were observed. The sample was stored for an additional two days and again, no solid particles were observed. Solvent was removed from the sample by storage under vacuum for 24 hours. No crystalline material was observed following removal of the solvent.

The present example yielded lercanidipine L-lactate. The resulting lercanidipine salt was subjected to elemental analysis; thermogravimetric analysis coupled to infra-red spectroscopy; and water content analysis. The lercanidipine salt also underwent physical testing using FT-Raman spectroscopy and was subjected to solubility testing. The results are described in Table 4, below.

Example 5

Preparation of Amorphous Salts and Attempts to Form Crystalline Lercanidipine Salts In addition to the salt screening experiments described in Example 5, single attempts to form crystalline lercanidipine salts were carried out for an additional twelve counterions: citrate, mucate, gentisate, gluconate, 2-oxo-glutarate, phosphate, saccharinate, salicylate, L-tartrate, terephtalate, malonate, and oxalate. A single attempt to form crystalline lercanidipine was made using each of the twelve counterions. None of the twelve counterions were capable of producing crystalline lercanidipine salts, and few of them produced characterized amorphous salts. The general experimental scheme used in screening each of the counterions is discussed in detail below. The choice of crystallization techniques was influenced by the known difficulty in obtaining crystalline lercanidipine and therefore, sufficient storage times and slow processes were chosen.

The final lercanidipine salts obtained from each of the salt screening experiments was dried completely and subjected to chemical and physical analysis. The chemical composition of each of the salt was determined using elemental analysis, thermogravimetric analysis coupled to infra-red spectroscopy, and water absorption analysis. The salts were also subjected to physical testing using FT-Raman spectroscopy and underwent solubility testing.

A stock solution of lercanidipine was prepared by dissolving 530 mg lercanidipine free base in 2.67 ml methanol (MeOH). To screen for crystal formation aliquots (0.1 ml) of lercanidipine stock solution were mixed with an acid as described in Table 5 below:

TABLE 4

| Salt form | Proposed formula | Elemental Analysis | TG-FTIR (mass loss) | FT Raman spectrum | Solubility in 0.1 N HCl |
| --- | --- | --- | --- | --- | --- |
| L-Lactate | $C_{36}H_{41}N_3O_6 \cdot C_3H_6O_3 \cdot 0.2MeOH$ | Calcd %: C 66.5, H 6.8, N 5.9<br>Found %: C 66.5, H 6.6, N 5.9 | 1% (MeOH) | agrees with proposed structure | 85 mg/L |

TABLE 5

| Sample No. | Lercanidipine Stock Solution: | Counterion: | Solvent: |
| --- | --- | --- | --- |
| 1 | 0.1 ml | 0.1258 ml aqueous citric acid (50 mg/ml) | 1 ml MeOH |
| 2 | 0.1 ml | 6.9 mg mucic acid | 0.1 ml $H_2O$/2 ml MeOH |

TABLE 5-continued

| Sample No. | Lercanidipine Stock Solution: | Counterion: | Solvent: |
|---|---|---|---|
| 3 | 0.1 ml | 5 mg gentisic acid | 0.1 ml $H_2O$/2 ml MeOH |
| 4 | 0.1 ml | 0.2570 ml aqueous gluconic acid (50 mg/ml) | 1.2 ml MeOH |
| 5 | 0.1 ml | 0.0955 ml aqueous 2-oxo-glutaric acid (50 mg/ml) | 0.0045 ml $H_2O$/1 ml MeOH |
| 6 | 0.1 ml | 0.0754 ml aqueous phosphoric acid (50 mg/ml) | 0.0246 ml $H_2O$/1 ml MeOH |
| 7 | 0.1 ml | 6 mg saccharin | 1.016 ml $H_2O$/1.2 ml MeOH |
| 8 | 0.1 ml | 0.1254 ml aqueous salicylic acid (50 mg/ml) | 1 ml MeOH |
| 9 | 0.1 ml | 0.0981 ml aqueous L-tartaric acid (50 mg/ml) | 0.0981 ml $H_2O$/1 ml MeOH |
| 10 | 0.1 ml | 5.5 mg terephtalic acid | 0.01 ml $H_2O$/1.4 ml MeOH |
| 11 | 0.1 ml | 0.0680 ml aqueous malonic acid (50 mg/ml) | 0.032 ml $H_2O$/1 ml MeOH |
| 12 | 0.1 ml | 0.0589 ml aqueous oxalic acid (50 mg/ml) | 0.0411 ml $H_2O$/1 ml MeOH |

Each of the samples of the present example were handled identically. After combining the lercanidipine free base and the corresponding counterion, the sample was allowed to stand closed at −18° C. for two days. After two days no precipitate was visible in any of the samples. The samples were then allowed to stand open under ambient conditions for 8 hours followed by storage at −18° C. for an additional 5 days. Again no precipitate was observed at the end of the storage period. The samples were then stored open under ambient conditions for 15 hours followed by an additional 2 days at −18° C. No precipitate was observed in any of the samples after storage. The solvent was removed from each of the samples under vacuum and the remaining solid was stored closed.

All of the attempts to form crystalline lercanidipine salts from lercanidipine free base and the counterions of the present example failed to produce any crystalline material. The present example, as well as experiments described in Example 5, demonstrate the difficulty and unpredictability of forming crystalline salts of lercanidipine.

The present example yielded two amorphous salts of lercanidipine; saccharinate and salicylate. Each amorphous lercanidipine salt was subjected to elemental analysis; thermogravimetric analysis coupled to infra-red spectroscopy; and water content analysis. Each amorphous lercanidipine salt also underwent physical testing using FT-Raman spectroscopy and was subjected to solubility testing. The results are described in Table 6, below.

Example 6

Chemical Composition of Amorphous and Crystalline Lercanidipine Salts

The elemental composition of both amorphous and crystalline lercanidipine salts was determined using dry combustion/thermal conductivity and non dispersive IR detection. Results of the elemental analysis are summarized in Table 7.

The residual solvent content of both amorphous and crystalline lercanidipine salts was determined using gravimetric analysis coupled with an infra-red (IR) spectrometer. A Netzsch Thermobalance TG-209 (Selb, Germany, Selb) in combination with a spectrometer FTIR Bruker Vector 22 (Fällanden, Switzerland) was used to for the analysis. The analysis were carried out according to the following conditions: 2-5 mg of sample heated in aluminum crucibles under nitrogen atmosphere at a heating rate of 10° C./minute from 25° C. to 250° C. Results of the gravimetric analysis are shown in Table 7.

The hygroscopicity of both amorphous and crystalline lercanidipine salts was determined by DVS analysis using a water absorption analyzer (Surface Measurement System Ltd., Marion, Buckinghamshire, UK). The analysis were carried out according to the following conditions: 10-15 mg of sample were placed on a quartz or platinum holder, the holder was placed in-turn on a microbalance, and the sample underwent humidity cycling between 0 and 95% relative humidity

TABLE 6

| Salt form | Proposed formula | Elemental Analysis | TG-FTIR (mass loss) | FT Raman spectrum | Solubility in 0.1 N HCl |
|---|---|---|---|---|---|
| Saccharinate | $C_{36}H_{41}N_3O_6 \cdot C_7H_5SO_3 \cdot 0.5MeOH$ | Calcd %: C 64.4, H 6.0, N 6.9, S 3.9 Found %: C 64.1, H 5.9, N 6.8, S 3.8 | 1.8% (MeOH) | agrees with proposed structure | 72 mg/L |
| Salicylate | $C_{36}H_{41}N_3O_6 \cdot C_7H_6O_3 \cdot 0.6MeOH$ | Calcd %: C 68.1, H 6.5, N 5.5 Found %: C 68.1, H 6.4, N 5.7 | 2.5% (MeOH) | agrees with proposed structure | |

(RH) at 25° C. (50-95-0-95-0-50% at a rate of 5% RH/hr). The results of the hygroscopicity analysis are summarized in Table 7 below.

TABLE 7

Chemical Composition of amorphous and crystalline lercanidipine salts

| Salt | Elemental Composition | Residual Solvent | Hygroscopicity |
|---|---|---|---|
| Amorphous besylate | $C_{42}H_{47}N_3O_9S$ | 2.8% (MeOH) | non-hygroscopic |
| Crystalline besylate | $C_{42}H_{47}N_3O_9S$ | 0.2% | non-hygroscopic |
| Crystalline napadisylate | $C_{82}H_{90}N_6O_{18}S_2$ | 3.7% (MeOH) | hygroscopic 0.4% $H_2O$ |

Example 8

Solubility of Crystalline and Amorphous Salts of Lercanidipine

The solubility of crystalline lercanidipine besylate, napadisylate and hydrochloride and amorphous lercanidipine besylate was evaluated by UV-Visible spectroscopy in aqueous 0.1 M HCl (pH 1) at 22° C. Suspensions of approximately 0.3 mg/ml of the respective compounds were prepared in an aqueous 0.1 M HCl and equilibrated by shaking for 24 hours. Following equilibration, the samples were filtered (0.1 μm filter) and the concentration was determined photometrically using Perkin Elmer Lambda 16 (Überlingen, Germany). Reference measurements were performed with 20% acetonitrile as a co-solvent.

TABLE 8

Solubility in 0.1 M HCl at 22° C.

| Salt | Solubility [mg/ml] | pH of solution |
|---|---|---|
| Crystalline hydrochloride | 10.0 | 1 |
| Crystalline besylate | 30.0 | 1 |
| Amorphous besylate | 155 | 1 |
| Crystalline napadisylate | 3.5 | 1 |

It can be seen from Table 8 that both crystalline besylate and napadisylate have lower solubility than the amorphous salt. It can also be seen from Table 2 that the solubility of the crystalline salts varies greatly and that crystalline besylate is substantially more soluble than either crystalline hydrochloride or napadisylate.

Example 6

Raman Spectra of Novel Lercanidipine Salts

The novel lercanidipine salts were analyzed using FT-Raman spectroscopy. A Bruker FT-Raman RFS 100 Spectrophotometer was utilized under the following typical conditions: about 10 mg sample (without any previous treatment), 64 scans 2 cm$^{-1}$ resolution, 100 mW laser power, Ge-detector.

The following Tables 9, 10 and 11 show the most significant peaks of Raman spectra for crystalline lercanidipine besylate and napadisylate, respectively, as well as amorphous lercanidipine besylate.

TABLE 9

Raman spectrum of crystalline lercanidipine besylate

| Wave number (cm$^{-1}$) | Peak intensity* |
|---|---|
| 86.1 | vs |
| 177.4 | m |
| 227.3 | m |
| 318.3 | m |
| 812.1 | m |
| 1002.3 | vs |
| 1035.5 | s |
| 1126.6 | m |
| 1162.0 | m |
| 1178.9 | m |
| 1197.5 | m |
| 1351.8 | vs |
| 1438.2 | m |
| 1448.4 | m |
| 1485.7 | s |
| 1533.9 | m |
| 1583.6 | s |
| 1609.9 | s |
| 1647.8 | s |
| 1683.0 | s |
| 2925.7 | s |
| 2956.0 | s |
| 2972.9 | m |
| 2991.1 | m |
| 3000.0 | m |
| 3023.3 | m |
| 3042.1 | m |
| 3064.0 | s |
| 3075.4 | s |

*m = moderate; s = strong, vs = very strong

TABLE 10

Raman spectrum of crystalline lercanidipine napadisylate

| Wave number (cm$^{-1}$) | Peak intensity* |
|---|---|
| 79.2 | vs |
| 96.4 | vs |
| 151.7 | s |
| 203.4 | m |
| 272.9 | m |
| 293.7 | m |
| 330.4 | m |
| 479.4 | m |
| 511.6 | m |
| 530.5 | m |
| 618.2 | m |
| 654.4 | m |
| 737.4 | m |
| 747.7 | m |
| 819.9 | s |
| 854.5 | m |
| 965.2 | m |
| 1001.4 | vs |
| 1033.4 | m |
| 1065.4 | m |
| 1089.0 | m |
| 1157.1 | m |
| 1173.3 | m |
| 1196.3 | s |
| 1248.4 | m |
| 1345.6 | vs |
| 1384.4 | m |
| 1400.8 | s |
| 1450.7 | m |
| 1462.5 | m |
| 1477.7 | s |
| 1519.8 | m |
| 1528.0 | m |
| 1572.0 | s |
| 1581.4 | s |

TABLE 10-continued

Raman spectrum of crystalline lercanidipine napadisylate

| Wave number (cm⁻¹) | Peak intensity* |
|---|---|
| 1603.1 | m |
| 1613.9 | m |
| 1648.6 | s |
| 1669.4 | vs |
| 2951.9 | s |
| 2985.2 | s |
| 2997.0 | s |
| 3025.5 | m |
| 3062.4 | s |

*m = moderate; s = strong, vs = very strong

TABLE 11

Raman spectrum of amorphous lercanidipine besylate

| Wave number (cm⁻¹) | Peak intensity* |
|---|---|
| 84.1 | vs |
| 146.6 | s |
| 269.0 | m |
| 314.4 | m |
| 617.4 | m |
| 727.4 | m |
| 816.1 | m |
| 827.9 | m |
| 997.7 | vs |
| 1001.5 | vs |
| 1017.2 | m |
| 1034.0 | m |
| 1124.3 | m |
| 1156.5 | m |
| 1185.8 | m |
| 1191.2 | m |
| 1196.4 | m |
| 1227.2 | m |
| 1348.4 | vs |
| 1384.6 | m |
| 1453.5 | m |
| 1492.0 | m |
| 1527.5 | m |
| 1580.3 | s |
| 1588.4 | m |
| 1603.9 | m |
| 1646.4 | s |
| 1673.9 | m |
| 1700.5 | m |
| 2932.2 | m |
| 2950.2 | m |
| 2980.8 | m |
| 3002.6 | m |
| 3052.4 | m |
| 3063.6 | s |

*m = moderate; s = strong, vs = very strong

Example 8

X-Ray Diffraction Patterns of Novel Crystalline Lercanidipine Salts

Figure 4:
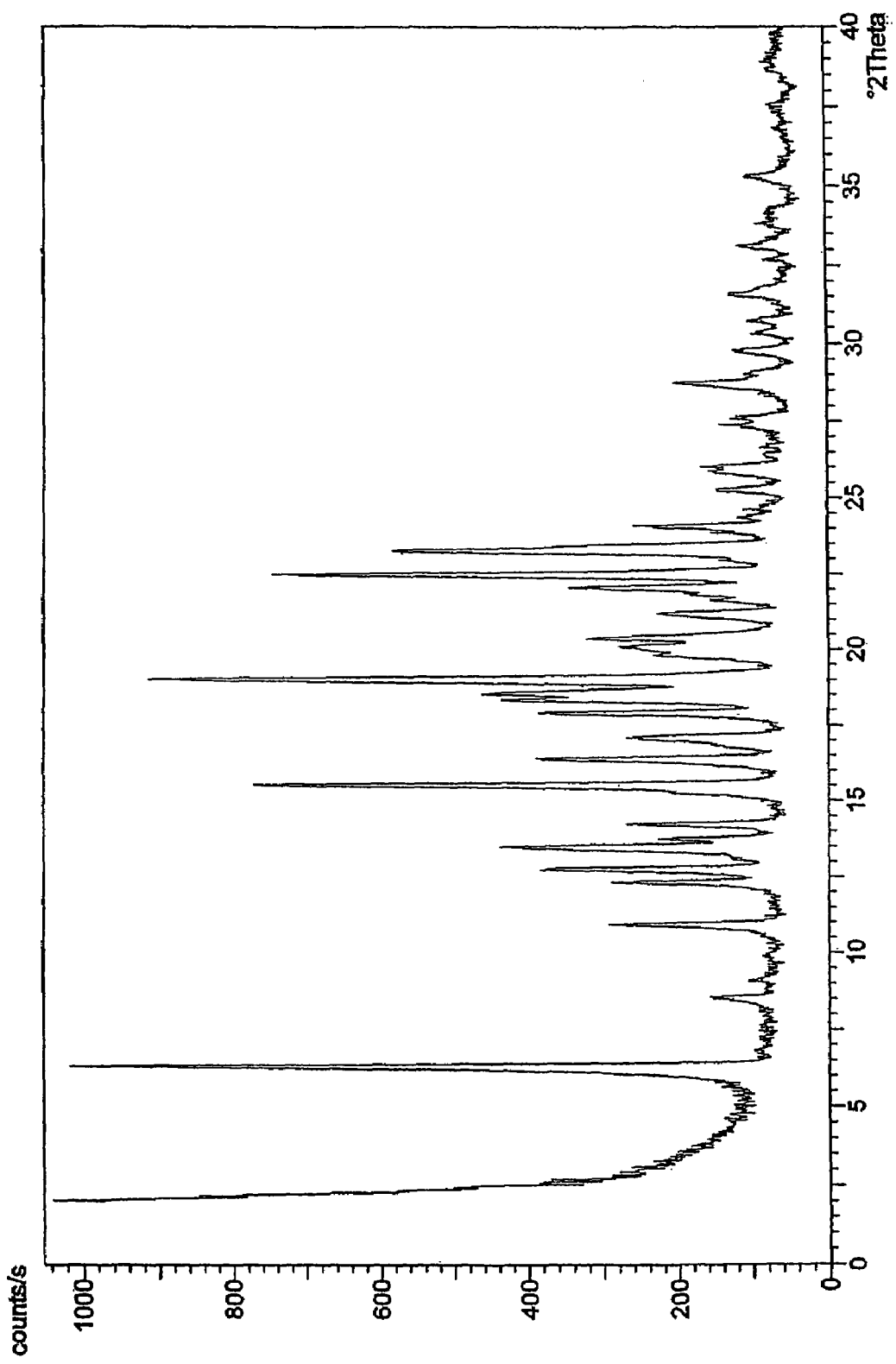
FIG. 4 depicts a X-Ray diffraction pattern of crystalline lercanidipine besylate.
Figure 5:
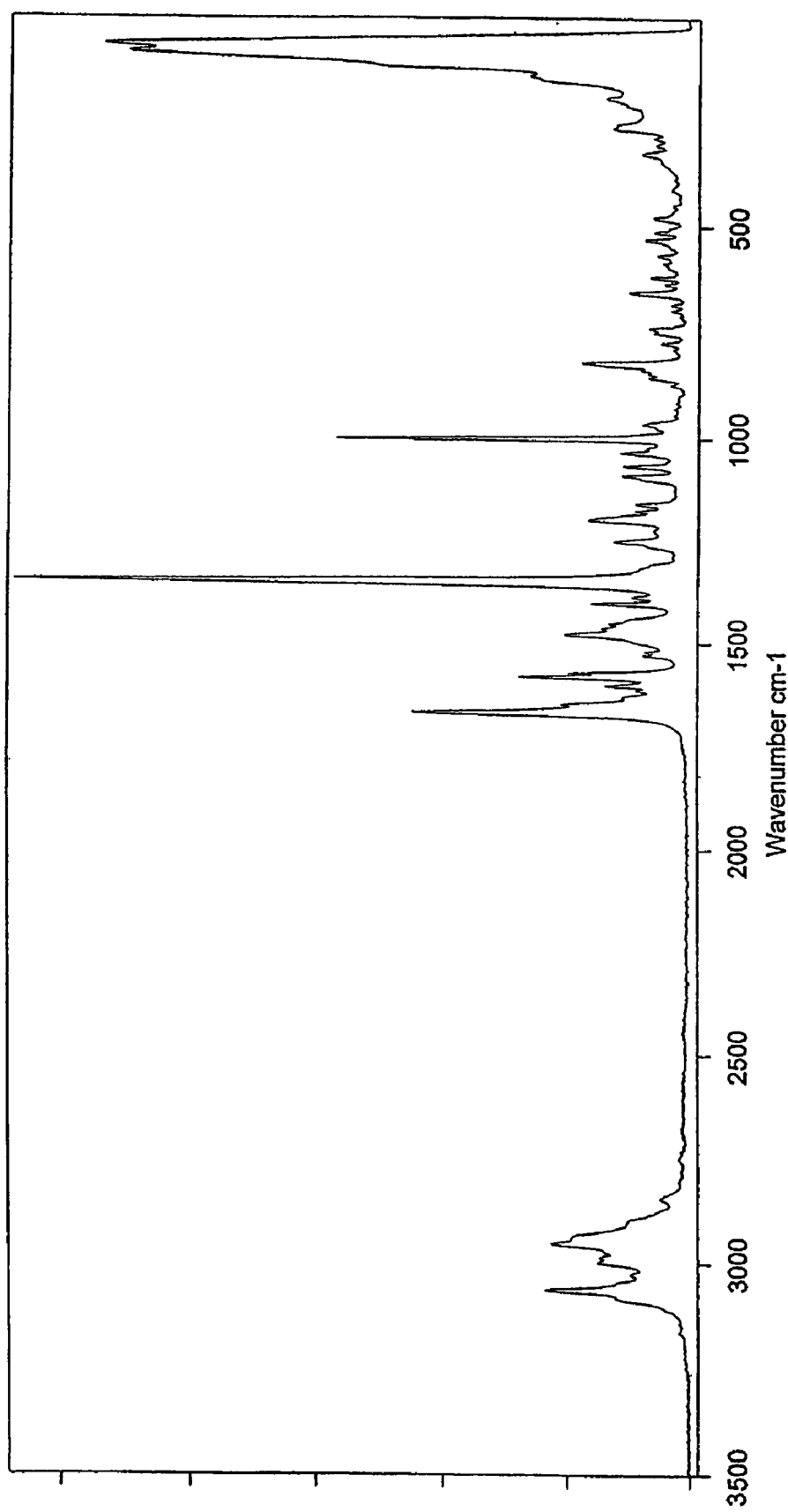
FIG. 5 depicts a FT-Raman pattern crystalline lercanidipine napadisylate.
Figure 6:
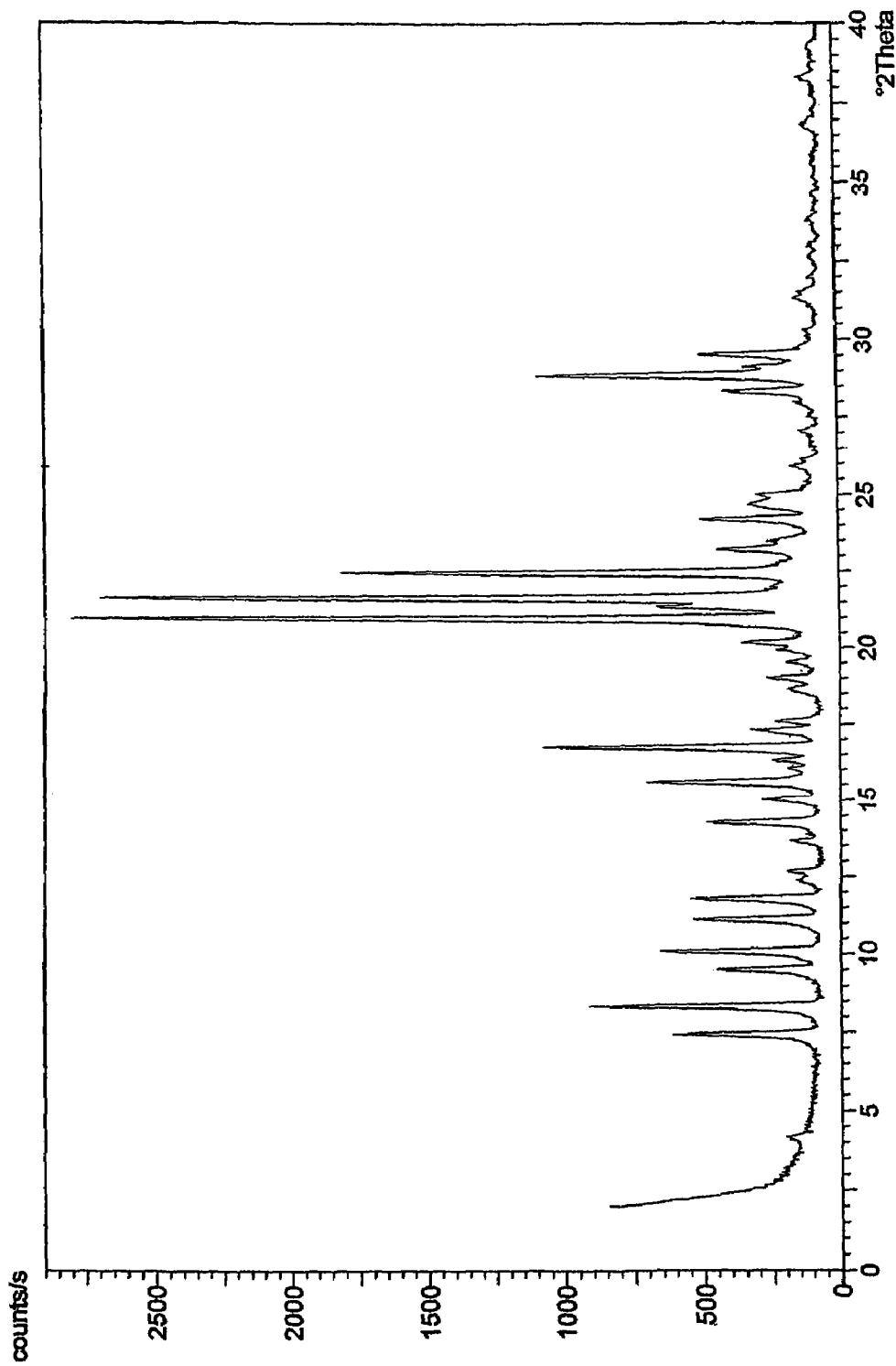
FIG. 6 depicts a X-Ray diffraction pattern of crystalline lercanidipine napadisylate.
Figure 7:
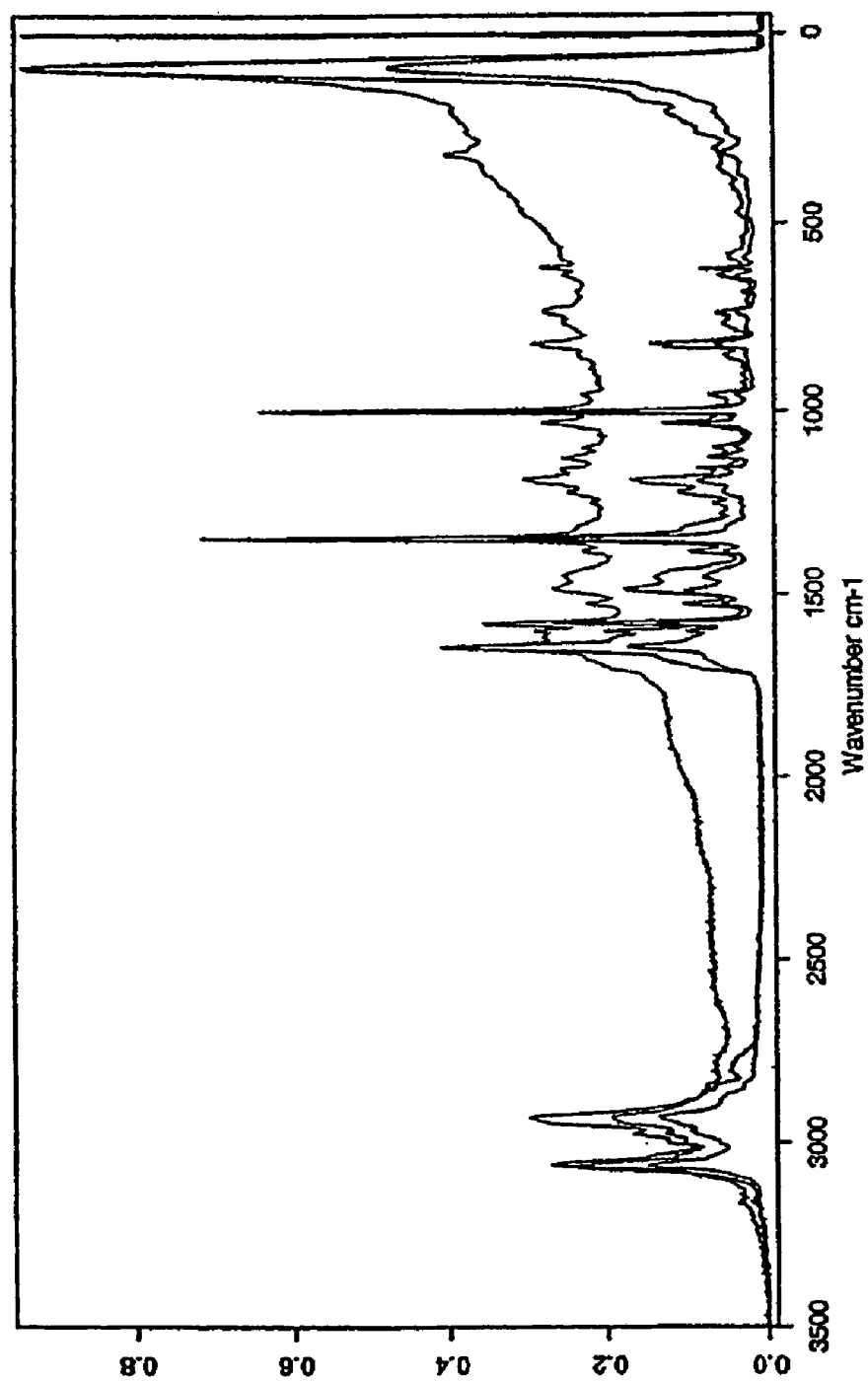
FIG. 7 depicts a FT-Raman pattern of comparing amorphous lercanidipine besylate to an equimolar solid state mixture of lercanidipine free base and benzenesulfonic acid.
Figure 8:
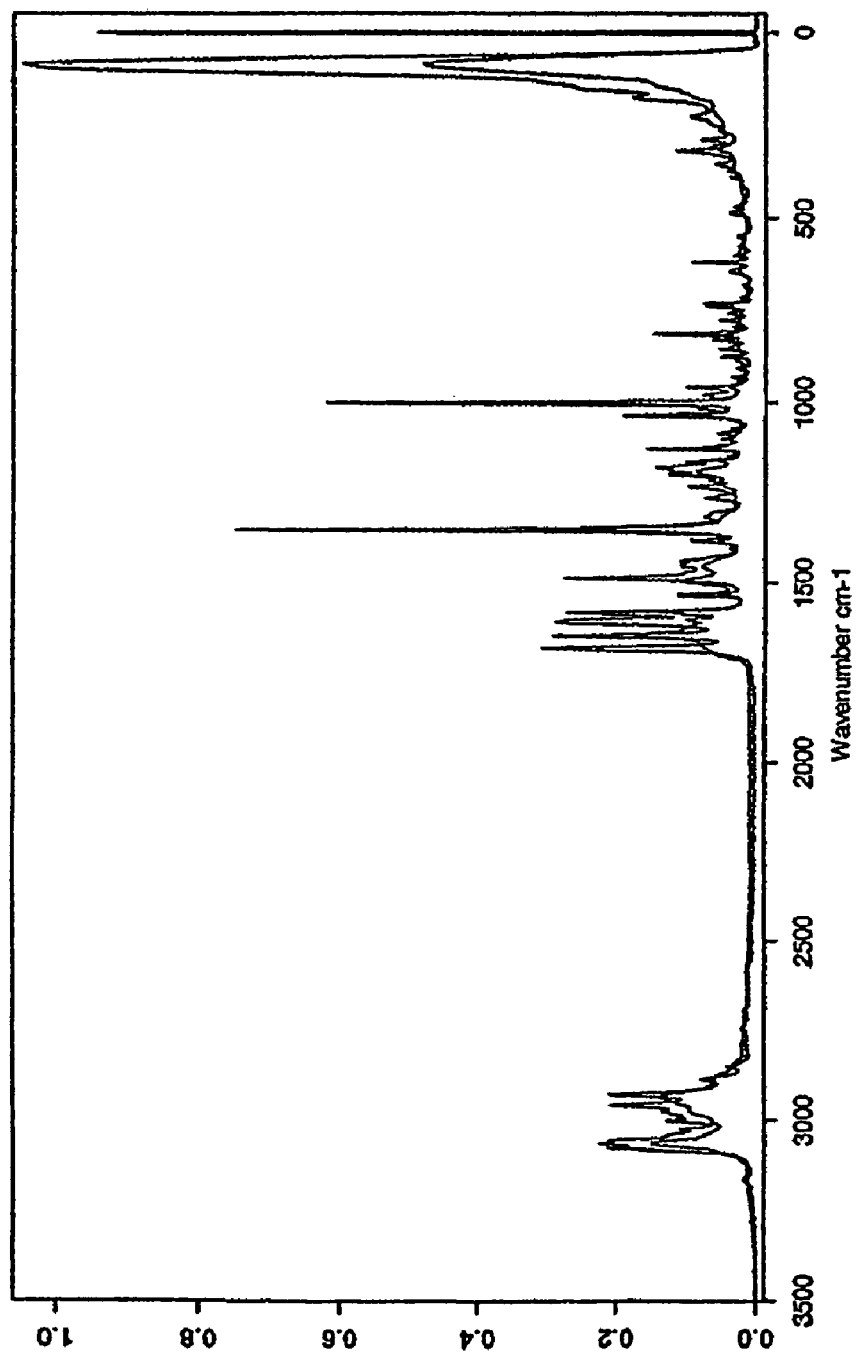
FIG. 8 depicts a FT-Raman pattern of comparing amorphous and crystalline lercanidipine besylate.

The X-ray diffraction pattern of crystalline lercanidipine besylate and napadisylate were obtained using a Philips X-pert PW 3040 or Philips PW 1710 powder difractometer (Eindhoven, Holland) under the following typical conditions: about 5-70 mg sample (without any previous treatment) with application of a slight pressure to obtain a flat sample, ambient air atmosphere and Copper Kα radiation, 0.02 °2θ, step size, 2 seconds per step, 2-50 °2θ. The obtained spectra are shown in FIGS. 4 and 6, and the corresponding main peaks are described in Tables 12 and 13. One skilled in the art will recognize that the 2θ values will generally be reproducible to within a range from about ±0.10 to about ±0.20 degrees, while the relative intensity of individuals peaks may vary from sample to sample. See, e.g, United States Pharmacopeia XXV (2002), pages 2088-2089.

TABLE 12

XRD of crystalline lercanidipine napadisylate

| D(Å) | Relative Intensity (I/Io) | 2 θ angle |
|---|---|---|
| 21.3 | 2 | 4.15 |
| 11.9 | 19 | 7.44 |
| 10.6 | 29 | 8.35 |
| 9.3 | 14 | 9.52 |
| 8.7 | 21 | 10.12 |
| 7.9 | 17 | 11.14 |
| 7.5 | 16 | 11.81 |
| 7.2 | 3 | 12.34 |
| 7.0 | 4 | 12.66 |
| 6.5 | 4 | 13.67 |
| 6.2 | 15 | 14.29 |
| 5.90 | 8 | 15.02 |
| 5.68 | 23 | 15.60 |
| 5.53 | 4 | 16.02 |
| 5.44 | 6 | 16.30 |
| 5.29 | 37 | 16.75 |
| 5.12 | 10 | 17.32 |
| 5.04 | 6 | 17.60 |
| 4.77 | 4 | 18.62 |
| 4.67 | 7 | 18.99 |
| 4.55 | 5 | 19.51 |
| 4.46 | 5 | 19.90 |
| 4.40 | 10 | 20.20 |
| 4.23 | 100 | 20.98 |
| 4.16 | 21 | 21.34 |
| 4.11 | 97 | 21.62 |
| 3.96 | 64 | 22.44 |
| 3.83 | 14 | 23.21 |
| 3.79 | 6 | 23.49 |
| 3.68 | 16 | 24.19 |
| 3.61 | 9 | 24.64 |
| 3.56 | 8 | 25.01 |
| 3.44 | 3 | 25.90 |
| 3.29 | 3 | 27.07 |
| 3.15 | 13 | 28.34 |
| 3.10 | 38 | 28.82 |
| 3.06 | 9 | 29.14 |
| 3.03 | 16 | 29.52 |
| 2.86 | 3 | 31.30 |
| 2.44 | 2 | 36.82 |
| 2.35 | 2 | 38.29 |

TABLE 13

XRD of crystalline lercanidipine besylate

| D(Å) | Relative Intensity (I/Io) | 2 θ angle |
|---|---|---|
| 14.0 | 100 | 6.31 |
| 10.4 | 7 | 8.54 |
| 9.7 | 2 | 9.13 |
| 8.1 | 24 | 10.92 |
| 7.2 | 21 | 12.31 |
| 6.9 | 34 | 12.77 |
| 6.6 | 39 | 13.50 |
| 6.5 | 17 | 13.73 |
| 6.2 | 22 | 14.23 |
| 5.71 | 77 | 15.52 |
| 5.41 | 36 | 16.40 |
| 5.18 | 19 | 17.12 |
| 4.95 | 34 | 17.92 |
| 4.85 | 40 | 18.30 |
| 4.78 | 43 | 18.55 |
| 4.67 | 93 | 19.00 |
| 4.49 | 17 | 19.78 |

TABLE 13-continued

XRD of crystalline lercanidipine besylate

| D(Å) | Relative Intensity (I/Io) | 2 θ angle |
|---|---|---|
| 4.42 | 23 | 20.08 |
| 4.36 | 29 | 20.35 |
| 4.18 | 16 | 21.24 |
| 4.03 | 31 | 22.07 |
| 3.96 | 72 | 22.47 |
| 3.83 | 53 | 23.22 |
| 3.79 | 29 | 23.45 |
| 3.70 | 19 | 24.05 |
| 3.53 | 10 | 25.24 |
| 3.45 | 10 | 25.81 |
| 3.42 | 11 | 26.04 |
| 3.26 | 7 | 27.36 |
| 3.23 | 6 | 27.62 |
| 3.11 | 16 | 28.73 |
| 3.00 | 7 | 29.77 |
| 2.95 | 4 | 30.32 |
| 2.91 | 4 | 30.74 |
| 2.84 | 8 | 31.52 |
| 2.74 | 3 | 32.70 |
| 2.71 | 6 | 33.09 |
| 2.54 | 6 | 35.32 |

Example 8

DSC Analysis of Crystalline Lercanidipine Besylate and Napadisylate

The melting points of the novel lercanidipine salts of the present invention and crystalline lercanidipine hydrochloride were analyzed using differential scanning calorimetry (DSC). DSC analysis measures changes that occur in a given sample with heating, wherein the changes identify transition phases. Enthalpy variations taking place in a transition phase are calculated on the basis of the area under the curve. The most common transition phases are melting and sublimation. The temperature at which transition starts, onset T, is given by the point in which the curve starts to deviate from the base line (flex point).

DSC of crystalline lercanidipine besylate: 4.040 mg of crystalline lercanidipine besylate was placed in a golden pan of the apparatus Perkin Elmer DSC7. The heating speed during the test was 10° C./min.

DSC crystalline lercanidipine napadisylate: 3.697 mg of crystalline lercanidipine napadisylate was placed in a golden pan of the apparatus Perkin Elmer DSC7. The heating speed during the test was 10° C./min.

Figure 2:
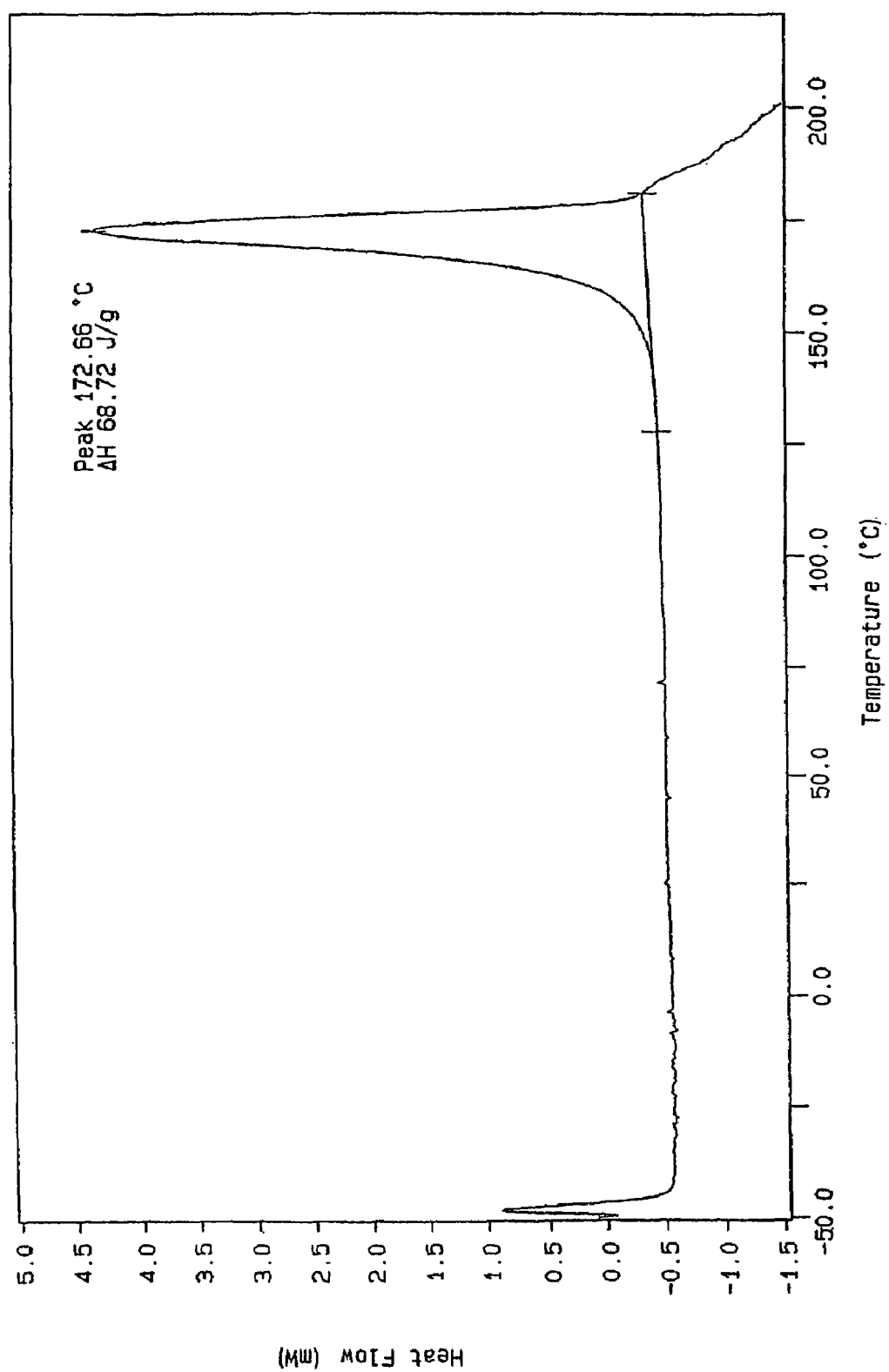
FIG. 2 depicts a differential scanning calorimetry profile for crystalline lercanidipine besylate.
Figure 3:
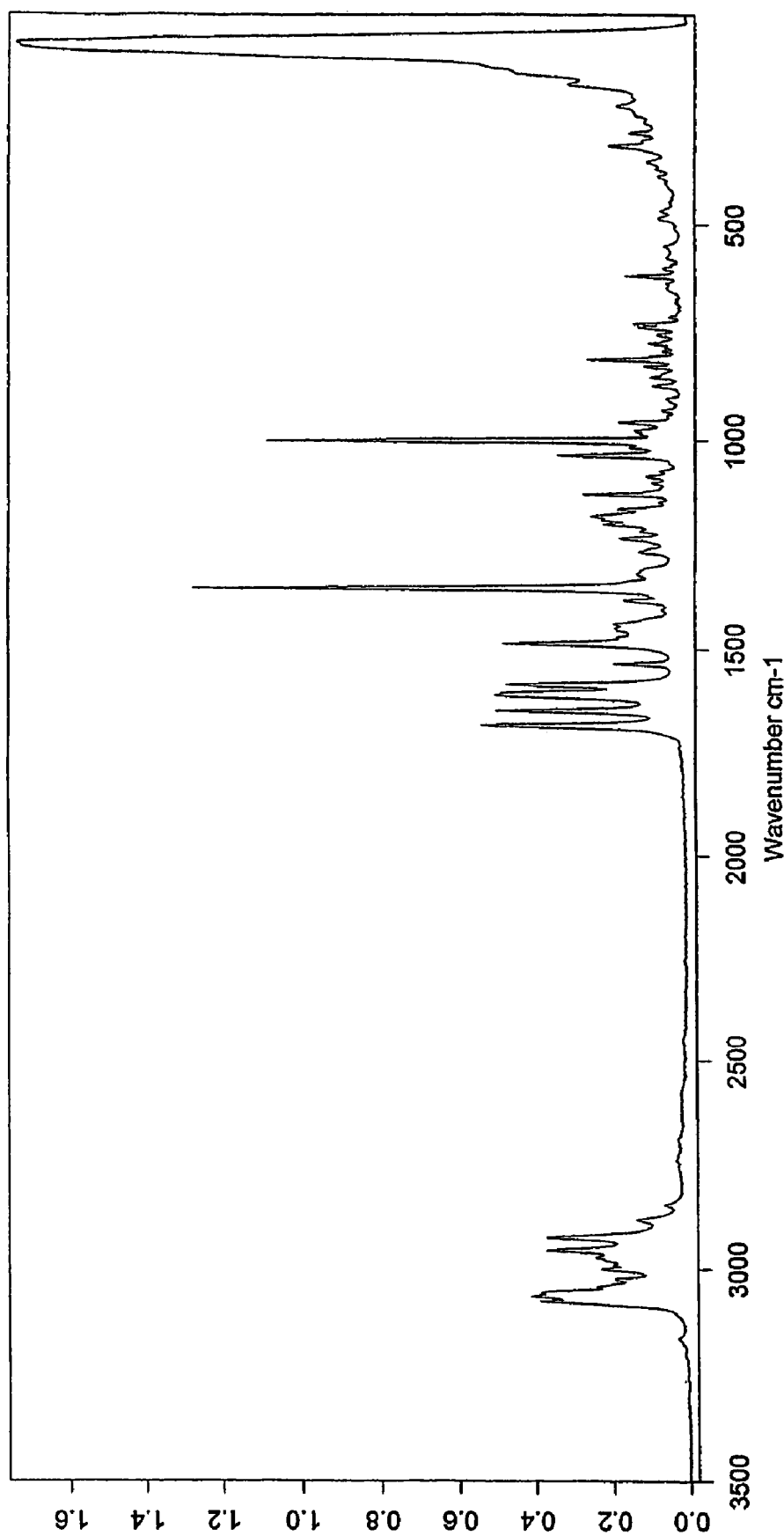
FIG. 3 depicts a FT-Raman pattern of crystalline lercanidipine besylate.

The data are shown in FIGS. 1 and 2 and the characteristic points of the figures are briefly summarized in Table 14.

TABLE 14

Melting point analysis by DSC

| Salt | Melting T (Tpeak) [° C.] | Onset T [° C.] |
|---|---|---|
| Crystalline Lercanidipine Besylate | 172.6 | 148.0 |
| Crystalline Lercanidipine Napadisylate | 149.8 | 98.0 |
| Crystalline Lercanidipine Hydrochloride Form (I) | 198.7 | 179.8 |
| Crystalline Lercanidipine Hydrochloride Form (II) | 209.3 | 169.0 |

All patents, applications, articles, statutes, and publications mentioned above are hereby incorporated by reference.

Many variations of the present invention will suggest themselves to those skilled in the art in light of the above detailed description. Such obvious variations are within the full intended scope of the appended claims.

We claim:

1. An acid addition salt of:
   (a) lercanidipine, and
   (b) an acid counterion of an acid selected from the group consisting of: (i) sulfonic acids, (ii) monocarboxylic acids, and (iii) aromatic sulfonimides, wherein the sulfonic acids are selected from the group consisting of benzenesulfonic acid and naphthalene-1,5-disulfonic acid.

2. The acid addition salt of claim 1, wherein said acid counterion is from a monocarboxylic acid selected from the group consisting of: (i) acetic acid, (ii) (+)-L- lactic acid, (iii) DL-lactic acid, (iv) DL-mandelic acid, (v) gluconic acid, (vi) cinnamic acid, (vii) salicylic acid, and (viii) gentisic acid.

3. The acid addition salt of claim 1, wherein said acid counterion is from saccharinic acid.

4. The acid addition salt of claim 1, wherein the acid counterion is from an acid selected from the group consisting of: L-lactic acid, cinnamic acid, salicylic acid, benzenesulphonic acid, naphthalene-1,5-disulphonic acid, and saccharinic acid, and wherein said salt is substantially amorphous.

5. The acid addition salt of claim 1, wherein the acid counterion is from an acid selected from the group consisting of: L-lactic acid, cinnamic acid, salicylic acid, benzenesulphonic acid, naphthalene-1,5-disulphonic acid, and saccharinic acid, and wherein said salt is substantially in the solvated amorphous form.

6. The acid addition salt of claim 1, wherein the acid counterion is from an acid selected from the group consisting of: L-lactic acid, cinnamic acid, benzenesulphonic acid, and naphthalene-1,5-disulphonic acid, and wherein said salt is in crystalline form and has a water content incorporated into the crystalline lattice of less than 4% (w/w).

7. The acid addition salt of claim 1, wherein the acid counterion is from an acid selected from the group consisting of: L-lactic acid, cinnamic acid, benzenesulphonic acid, and naphthalene-1,5-disulphonic acid, and wherein said salt is in crystalline form and has a residual solvent content incorporated into the crystalline lattice of less than 4% (w/w).

8. The acid addition salt of claim 1, wherein the acid counterion is from an acid selected from the group consisting of: L-lactic acid, cinnamic acid, salicylic acid, benzenesulphonic acid, naphthalene-1,5-disulphonic acid, and saccharinic acid, and wherein said salt is substantially pure.

9. The acid addition salt of claim 1 in the form of a solvate, and wherein the acid counterion is from an acid selected from the group consisting of: L-lactic acid, cinnamic acid, salicylic acid, benzenesulphonic acid, naphthalene-1,5- disulphonic acid, and saccharinic acid.

10. The acid addition salt of claim 1 in the form of a hydrate, and wherein the acid counterion is from an acid selected from the group consisting of: L-lactic acid, cinnamic acid, salicylic acid, benzenesulphonic acid, naphthalene-1,5-disulphonic acid, and saccharinic acid.

11. An acid addition salt of:
    (a) lercanidipine, and
    (b) an acid counterion of an acid selected from the group consisting of: (i) benzenesulfonic acid, and (ii) naptha-lene-1,5-disulfonic acid.

12. The acid addition salt of claim 11, wherein said counterion is from benzenesulfonic acid.

13. The acid addition salt of claim 11, wherein said counterion is from napthalene-1,5-disulfonic acid.

14. The acid addition salt of claim 12, wherein said salt is substantially crystalline.

15. The acid addition salt of claim 13, wherein said salt is substantially crystalline.

16. The acid addition salt of claim 12, wherein said salt is substantially amorphous.

17. The acid addition salt of claim 14, said salt having the physical properties:
   (i) a melting point between from about 170° C. to about 175° C. as determined by DSC; and
   (ii) a solubility from about 25 mg/L to about 35 mg/L in 0.1 M HCl at 22° C.

18. The acid addition salt of claim 15, said salt having the physical properties:
   (i) a melting point from about 145° C. to about 155° C. as determined by DSC; and
   (ii) a solubility from about 3 mg/L to about 4 mg/L in 0.1 M HCl at 22° C.

19. The acid addition salt of claim 16, said salt having the physical properties:
   (i) a glass transition temperature from about 54° C. to about 61° C. as determined by DSC; and
   (ii) a solubility from about 150 mg/L and about 160 mg/L in 0.1 M HCl at 22° C.

20. A crystalline lercanidipine napadisylate having a x-ray diffraction pattern comprising four or more peaks with a 2θ value selected from the group consisting of: 8.35, 10.12, 11.14, 11.81, 14.29, 15.60, 16.75, 20.98, 21.34, 21.62, 22.44, 23.21, 24.19, 28.82 and 29.52.

21. The crystalline lercanidipine napadisylate of claim 20 having a x-ray diffraction pattern comprising four or more peaks with a 2θ value selected from the group consisting of: 8.35, 10.12, 15.60, 16.75, 20.98, 21.34, 21.62, 22.44, 24.19, and 28.82.

22. The crystalline lercanidipine napadisylate of claim 20 having a x-ray diffraction pattern comprising four or more peaks with a 2θ value selected from the group consisting of: 8.35, 16.75, 20.98, 21.62, 22.44, and 28.82.

23. The crystalline lercanidipine napadisylate of claim 20 having a x-ray diffraction pattern comprising six or more peaks with a 2θ value selected from the group consisting of: 8.35, 10.12, 11.14, 11.81, 14.29, 15.60, 16.75, 20.98, 21.34, 21.62, 22.44, 23.21, 24.19, 28.82 and 29.52.

24. The crystalline lercanidipine napadisylate of claim 20 having a x-ray diffraction pattern comprising eight or more peaks with a 2θ value selected from the group consisting of: 8.35, 10.12, 11.14, 11.81, 14.29, 15.60, 16.75, 20.98, 21.34, 21.62, 22.44, 23.21, 24.19, 28.82 and 29.52.

25. A crystalline lercanidipine besylate having a x-ray diffraction pattern comprising four or more peaks with a 2θ value selected from the group consisting of: 6.31, 10.92, 12.31, 12.77, 13.50, 13.73, 14.23, 15.52, 16.40, 17.12, 17.92, 18.30, 18.55, 19.00, 19.78, 20.08, 20.35, 21.24, 22.07, 22.47, 23.22, 23.45, 24.05, and 28.73.

26. The crystalline lercanidipine besylate of claim 25 having a x-ray diffraction pattern comprising four or more peaks with a 2θ value selected from the group consisting of: 6.31, 10.92, 12.31, 12.77, 13.50, 13.73, 15.52, 16.40, 17.92, 18.30, 18.55, 19.00, 20.08, 20.35, 22.07, 22.47, 23.22, and 23.45.

27. The crystalline lercanidipine besylate of claim 25 having a x-ray diffraction pattern comprising four or more peaks with a 2θ value selected from the group consisting of: 6.31, 12.77, 13.50, 15.52, 17.92, 18.30, 18.55, 19.00, 20.35, 22.07, 22.47, 23.22, and 23.45.

28. The crystalline lercanidipine besylate of claim 25 having a x-ray diffraction pattern comprising four or more peaks with a 2θ value selected from the group consisting of: 6.31, 12.77, 13.50, 15.52, 17.92, 18.30, 18.55, 19.00, 22.07, 22.47, and 23.22.

29. The crystalline lercanidipine besylate of claim 25 having a x-ray diffraction pattern comprising six or more peaks with a 2θ value selected from the group consisting of: 6.31, 12.77, 13.50, 15.52, 17.92, 18.30, 18.55, 19.00, 20.35, 22.07, 22.47, 23.22, and 23.45.

30. The crystalline lercanidipine besylate of claim 25 having a x-ray diffraction pattern comprising eight or more peaks with a 2θ value selected from the group consisting of: 6.31, 12.77, 13.50, 15.52, 17.92, 18.30, 18.55, 19.00, 20.35, 22.07, 22.47, 23.22, and 23.45.

31. A method for preparing lercanidipine crystalline salts, comprising the steps of:
   (b) reacting methyl 1,1,N-trimethyl-N-(3,3-diphenylpropyl)-2-aminoethyl 1,4-dihydro-2,6-dimethyl-4-(3-nitrophenyl)-pyridine-3,5-dicarboxylate, with an acid counterion in an organic solvent to form a lercanidipine salt, wherein said acid counterion is selected from the group consisting of: L-lactic acid, cinnamic acid, benzenesulphonic acid, and naphthalene- 1,5-disulphonic acid;
   (c) removing said organic solvent, thereby isolating the resultant lercanidipine salt; and
   (d) recrystallizing said lercanidipine salt in at least one of two successive steps, regardless of sequence, from a solution of said lercanidipine salt in;
   (i) an aprotic solvent; and
   (ii) a protic solvent;
   thereby isolating methyl 1,1, N-trimethyl-N-(3,3-diphenylpropyl)-2-aminoethyl 1,4-dihydro-2,6-dimethyl-4-(3-nitrophenyl)-pyridine-3,5-dicarboxylate as a substantially pure crystalline salt.

32. The method of claim 31, wherein said acid counterion is from benzenesulfonic acid.

33. The method of claim 31, wherein said acid counterion is from napthalene-1,5-disulfonic acid.

34. The method of claim 31, further comprising the step of seeding said lercanidipine salt with a crystalline lercanidipine salt.

* * * * *